United States Patent [19]

Shore

[11] Patent Number: 5,128,655
[45] Date of Patent: Jul. 7, 1992

[54] FLEXION MONITORING DEVICE

[76] Inventor: Edward E. Shore, 4346 Washington Irving Rd., Fort Worth, Tex. 76114

[21] Appl. No.: 639,110

[22] Filed: Jan. 9, 1991

[51] Int. Cl.⁵ .............................................. G08B 21/00
[52] U.S. Cl. ................... 340/573; 128/782; 200/61.52; 200/DIG. 2; 340/689
[58] Field of Search ............... 340/573, 689; 200/61.52, DIG. 2; 128/782

[56] References Cited

U.S. PATENT DOCUMENTS

| | | | |
|---|---|---|---|
| 3,582,935 | 6/1971 | Verhaeghe | 340/573 |
| 4,617,525 | 10/1986 | Lloyd | 340/573 |
| 4,871,998 | 10/1989 | Chaillou | 340/573 |
| 4,958,145 | 9/1990 | Morris | 340/689 |

Primary Examiner—Glenn R. Swann, III
Attorney, Agent, or Firm—John E. Vandigriff

[57] ABSTRACT

The invention is a monitoring device used to monitor bending of the back and spinal column that counts and displays the number of bends of the back beyond a predetermined angle during a specified time of operation, and also provides the option to emit an audible tone each time the predetermined angle is exceeded.

7 Claims, 3 Drawing Sheets

Position 3
Counter

Position 1
Off

Position 2
Counter/Alert

FLEXION MONITORING DEVICE

FIELD OF THE INVENTION

This invention relates to monitoring devices, and more particularly to a battery powered device for determining change-of-body position as a result of forward bending, or flexion of the wears's spinal column.

BACKGROUND OF THE INVENTION

Heretofore, attempts have been made to solve the problems related to low back injuries and pain through the use of posture correcting devices such as those defined in U.S. Pat. No. 3,582,935 to Verhaeghe, entitled Posture Control and Correcting Device, issued in 1986, and U.S. Pat. No. 4,871,998 to Chaillou entitled Posture Belt, issued in 1988. The devices of these patents serve the purpose for which they were intended, alerting the wearer that his posture is incorrect, but the devices do not inform the wear what is needed to correct posture.

Posture control cannot be accomplished by a device limited to the function of warning the wearer that he is exhibiting improper posture, because once the warning is emitted, it is lost and is not recorded. To be accurate, research must be capable of detecting (counting) the frequency of improper bending/lifting, and storing the data for later study.

BRIEF SUMMARY OF THE INVENTION

The invention is a device for detecting and recording the frequency of change-of-body position as a result of forward bending, or flexion of the wear's spinal column. Such a device is useful in preventing of cumulative and musculoskeletal injuries resulting from improper bending and lifting among industrial workers.

The flexion monitoring device includes a three position switch having an off position, a counting position, and counting and alerting position. A pair of position sensitive switches are used in conjunction with the three position switch, an LCD counter, and an audible tone device.

In one position of the switch, one of the position sensitive switches causes the counter to increment each time the wear bends improperly, recording an incident of improper bending or lifting.

In a second position of the three position switch, a second position sensitive switch causes an alert device to emit an audible tone each time the wear bends improperly.

The Flexion device is self-contained, change-of-body-position responding, electronic powered by a battery source, and provides two functions resulting from forward bending, or flexion of the wear's spinal column.

The first function utilizes a liquid crystal display electron counting module activated by a switching device that detects a change of position of the flexion monitoring device when worn on the wearer's back. The switching device is mounted so that it will activate the counter when the wearer, reaching a predetermined degree of positioned change. The purpose being to gather and store data representing the accumulated frequency that a predetermined degree of movement of the human spinal column occurs while involved in forward and downward bending in the sagittal plane about a frontal horizontal axis. This is accomplished by attaching the flexion monitoring device to the spinal column by a harness worn by a person during the course of activities while working.

The second function includes the first function of counting, and at the same time alerting the wearer of the monitoring device that they are bending in a fashion that could be putting themselves in jeopardy of cumulative trauma and musculoskeletal injury.

The separate functions are controlled though use of a three position key lock switch. The three positions are Counter, Counter/alert and Off. The key is removable in all three positions once the desired function is selected, to prevent inadvertent loss of data and the audible warning signal.

The technical advance represented by the invention as well as the objects thereof will become apparent from the following description of a preferred embodiment of the invention when considered in conjunction with the accompanying drawings, and the novel features set forth in the appended claims.

DESCRIPTION OF A PREFERRED EMBODIMENT

Figure 1:
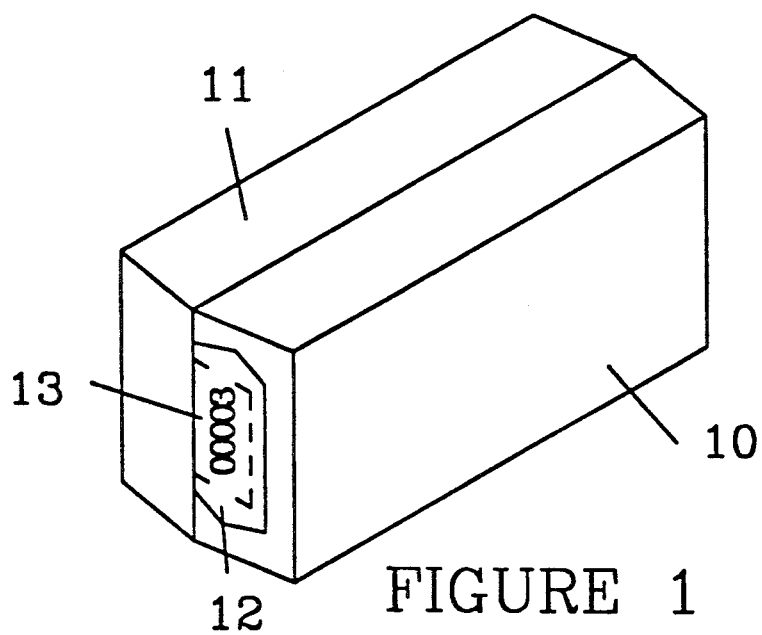
FIG. 1 illustrates the Flexion device.

FIG. 1 illustrates one embodiment of the Flexion device. A two part housing has a front part 10 and a rear part 11. The two part housing is, for example, a molded high impact plastic. A clear viewing window 12 is in one end of part 10. Window 12 is of a clear scratch resistant acrylic plastic.

a liquid crystal display (LCD) electronic counting module 13 is visible through window 12, and is mounted in the housing behind window 12. The electronic counting module is a digital counting module with a counting range of from 0 to 99999. The counting module is constructed around a CMOS monolithic integrated circuit epoxy-mounted directly on the module's printed circuit board. The module may be, for example, an Archer P/N 277-302. The counting module has five pins, three of which are used in the present invention. The pins used are: Pin 1, Ground or 1.5 volt negative; Pin 3, counting input; and pin 4, 1.5 volt positive. The operation of the counting module will be described in more detail below with reference to FIG. 7.

Figure 2:
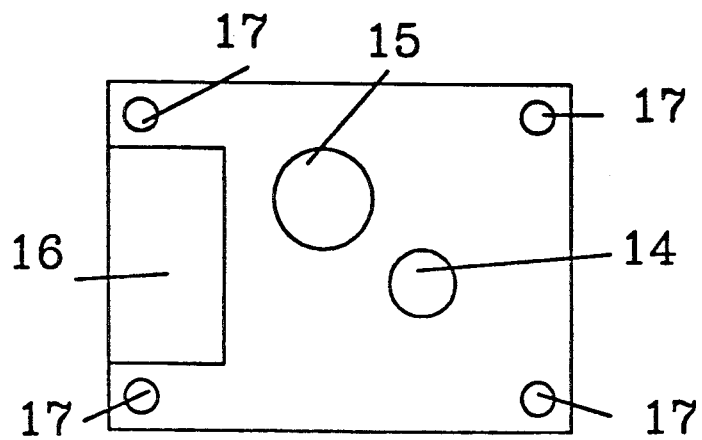
FIG. 2 is a rear view of the Flexion device.

FIG. 2 is rear section 11 of the housing. Locations of various components of the invention are indicated. A key lock 14 is shown. Key lock 14 is used to turn the monitor on and off and to lock other settings in place. Lock 14 is a three position key lock, for example, a "Y" series Switchlock P/N Y200AA2C203NQ double pole switch with three key pull positions, manufactured by C&K Components, Inc. Clayton, NC.

An audible warning device 15 is mounted adjacent the key switch 14. Device 15 is a sound emitting device, for example, a sonalert solid-State audible Warning Device, Mallory P/N SC628.

A nine volt battery 16 is shown mounted adjacent to sound emitting device 15.

Figure 3:
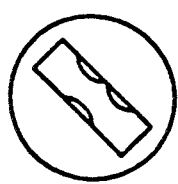
FIG. 3 illustrates the switch in three different positions.
Figure 3:
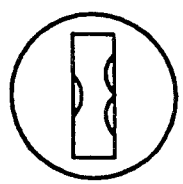
Figure 3:
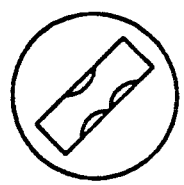

FIG. 3 illustrates the three possible positions of switch 14. Position 1 is the Off position. Position 2 is the "ON" position for both the counter and the alert, sound emitting device. Position 3 is the "ON" position for the counter only.

Figure 4:
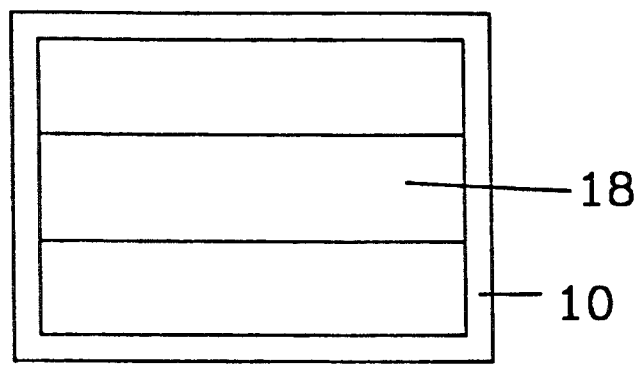
FIG. 4 is a front view of the Flexion device.

FIG. 4 shows the front part 10 of the device housing. A strip 18 of Velcro is attached to front 10. Velcro 18 is used for attaching the monitor device to a wear's harness. The harness, not illustrated, also has a strip of Velcro to which strip 18 is attached.

Figure 5:
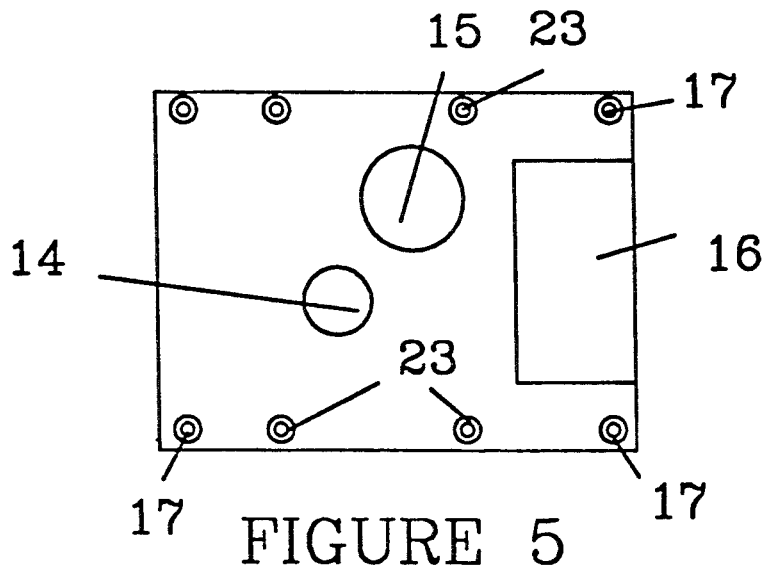
FIG. 5 is a rear interior view of the flexion device.

FIG. 5 shows the interior of housing part 11, and the component arrangement attached to part 11. Three position switch 14 is mounted through part 11, with contact of the switch in the box and the key side of the lock out side the housing. Key switch 14 has eight contacts, which will be explained in more detail with reference to FIG. 7. A nine volt batter 16 is mounted on the part 11 along with Sonalert Warning Device 15. Four screw holes 17 are used to attach part 11 to part 10 of the housing.

Figure 6:
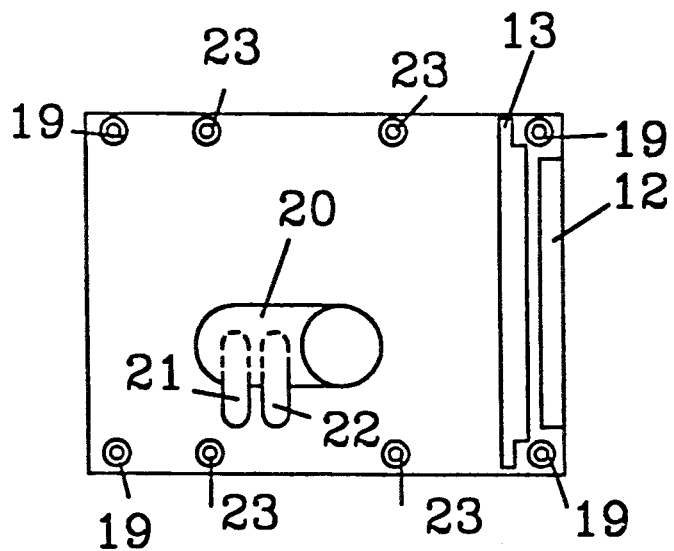
FIG. 6 is a front interior view of the flexion device.

FIG. 6 shows the interior side of part 10 of the housing, and the components mounted thereon. Viewing window 12 is mounted at one end of part 10. Counter 13 is mounted adjacent window 12 such that the LCD counting module may be viewed through window 12. Counting module is held in place, for example, with epoxy cement. A mount 20 is used to mount two mercury switches 21 and 22. Mount 20 may be, for example, a pine wood dowel one inch in diameter and about 1.25 inches long. Two holes, not illustrated, approximately 0.33438 inch in diameter are drilled in the dowel for receiving the mercury switches 21 and 22. Each mercury switch may be, for example, a simple single-pole/-single throw switch, Archer P/N 275-027, sold by Tandy Corp., Fort Worth, Tex. Holes 19 are used in conjunction with holes 17, FIG. 5, for hold the two parts 10, 11 of the device housing together.

Figure 7:
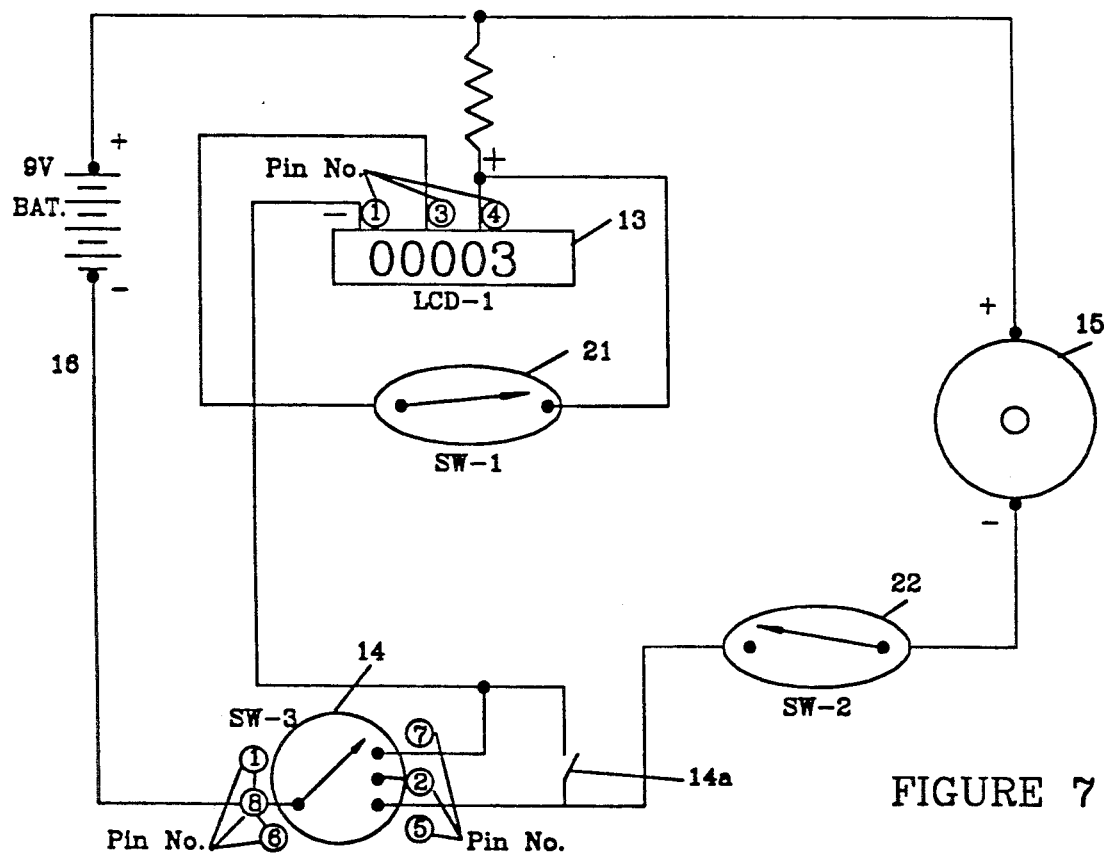
FIG. 7 is a schematic diagram of the circuitry of the flexion device.

FIG. 7 is a schematic diagram of the monitoring device. Three position switch 14, SW-3, includes terminals 1, 6, 8 and 2, 5 and 7. Pins 1, 6 and 8 are connected to the negative terminal of 9 volt battery 16. When switch 14 is contacting pin 7, a negative 9 volts is applied to terminal 1 of LCD 13. Positive 9 volts is applied to terminal 4 of LCD 13 through resistor R1. Connected between terminals 4 and 3 of LCD 13 is a position sensitive mercury switch 21. When the wearer of the flexion device is standing upright, switch 21 is open. Each time the wearer bends forward in a rotational movement from the vertical, or upright posture position, to an improper bending position, mercury switch 21 closes, completing the circuit between terminals 4 and 3 of LCD counter 13. The amount of forward bend is predetermined and may be, for example 45 degrees. The amount of predetermined bending necessary to close switch 21 may be varied depending upon frequency of bending to a specified angle. Each time switch 21 is closed, LCD counter is advanced one count. Therefore, during a specified period, the number of improper bending motions are recorded.

When switch 14 connected to, terminal 5, nine volts negative is applied to LCD counter 13 pin 1 and also to switch 22. Switch 14a is an integral part of Switch 14 and applies negative 9 volts to both LCD 13 and switch 22 when switch 14 is at position 5.

Switch 22 is a position sensitive mercury switch similar to switch 21, and closes when switch 21 closes. When switch 22 closes, the negative nine volts is applied to Warning/alert device 15. Positive terminal of device 15 is connected to the positive terminal of battery 16. When the wearer of the flexion monitoring device bends forward the predetermine amount, switch 22 and switch 21 close. The closure of switch 21 advances counter 13 one count, and the closure of switch 22 completes the circuit to warning/alert device 15 causing it to emit and audible sound. This audible sound alerts the wear that he is improperly bending.

When switch 14 is at terminal 2, the monitoring device is turned off. When switch 14 is at each of the positions, counter on, counter/alert on, and off, the key, not illustrated, used to turn the switch, may be removed to prevent accidental movement of the switch from a predetermined position.

I claim:

1. a flexion monitoring device comprising:

a two part electronic components housing having a section for mounting a counting means for gathering and storing data to determine the extent of improper forward bending of the low back, with said counting means being located interiorly in one end of said section;

a switching means, mounted interiorly in said front section to sense a predetermined degree of flexion of said low back and to supply an activating electrical signal to said counting means on each event wherein said predetermined degree of flexion of said low back is reached;

a viewing means located on the same end of said front section as said counting means to permit observing of an accumulated count upon said counting means from the exterior of said front section;

a rear section of said two part electronics components housing for mounting an electric battery power source interiorly in its own separate compartment;

a warning means mounted interiorly in said rear section, with its sound emitting portion protruding exteriorly, to alert the water of said flexion monitoring device of said improper forward bending of the low back, through activation by said electrical signal from said switching means located in said front section;

a voltage reducing means located between the positive source of said electrical battery power source and the positive input to said counting means; and a function selector key locking means mounted interiorly in said rear section with its key receptacle protruding exteriorly for selecting either a counting function or a counting and warning function combined.

2. A flexion monitoring device attachable to the spinal column of a person for monitoring the frequency of bending of the lower back, comprising:

a counting circuit;

a position sensitive switch connected to and advancing said counting circuit each time the lower back is bent through a predetermined angle; and a display device for displaying the number of counts registered by said counting circuit indicative of the number of times the lower back is bent through said predetermined angle.

3. The monitoring device of claim 2, including:

a warning device capable of emitting an audible signal; and a second position sensitive switch connected to and energizing said warning device to cause it to emit an audible signal each time the lower back is bent through a predetermined angle.

4. The monitoring device according to claim 3, including a key switch for switching the monitoring device between off and two operating modes.

5. The monitoring device according to claim 4, wherein said two operating modes are: (1) counting each time the lower back is bent though a predetermined angle; and (2) counting as in (1), and also emitting an audible tone each time the lower back is bent though a predetermined angle.

6. A flexion monitoring device attachable to the spinal column of a person for monitoring the frequency of bending of the lower back, comprising:
   a counting circuit;
   a position sensitive switch connected to and advancing said counting circuit each time the lower back is bent through a predetermined angle;
   a display device for displaying the number of counts registered by said counting circuit indicative of the number of times the lower back is bent through a predetermined angle;
   a warning device capable of emitting an audible signal; and
   a second position sensitive switch connected to and energizing said warning device to cause it to emit and audible signal each time the lower back is bent through said predetermined angle.

7. The monitoring device according to claim 6, including a key switch for switching the monitor device between off and two operating modes, wherein said two operating modes are: (1) counting each time the lower back is bent though a predetermined angle; and (2) counting as in (1), and also emitting an audible tone each time the lower back is bent through a predetermined angle.

* * * * *